United States Patent [19]

Suenaga et al.

[11] 4,313,093
[45] Jan. 26, 1982

[54] LASER DEVICE

[75] Inventors: Norihiro Suenaga, Tokyo; Seiji Sugiyama, Sohka; Nobuyuki Suenaga, Shizuoka, all of Japan

[73] Assignee: Nippon Infrared Industries Co., Ltd., Japan

[21] Appl. No.: 131,428

[22] Filed: Mar. 18, 1980

[30] Foreign Application Priority Data

Mar. 23, 1979 [JP] Japan .................... 54-33194

[51] Int. Cl.³ ............................... H01S 3/00
[52] U.S. Cl. ....................... 331/94.5 D; 128/303.1; 219/121 L; 219/121 LM
[58] Field of Search ............ 128/303.1, 395, 396; 331/94.5 D, DIG. 1; 219/121 L, 121 LV, 121 LU, 121 LG, 121 LM; 362/390

[56] References Cited

U.S. PATENT DOCUMENTS

| | | | |
|---|---|---|---|
| 1,145,382 | 7/1915 | Mc Williams | 362/390 |
| 1,802,589 | 4/1931 | Thompson | 362/390 |
| 3,858,122 | 12/1974 | Angelbeck et al. | 331/94.5 D |
| 3,913,582 | 10/1975 | Sharon | 128/303.1 |
| 4,143,660 | 3/1979 | Malyshev et al. | 128/303.1 |

FOREIGN PATENT DOCUMENTS 2815458 10/1978 Fed. Rep. of Germany ..... 331/94.5

OTHER PUBLICATIONS

Polanyi et al., A $CO_2$ Laser for Surgical Research Med. & Biol. Engng., vol. 8, No. 6, pp. 541–548, Perg. Press, 1970.

*Primary Examiner*—Robert W. Michell
*Assistant Examiner*—Arthur S. Rose
*Attorney, Agent, or Firm*—Toren, McGeady & Stanger

[57] ABSTRACT

A laser device particularly suitable for use in surgery includes a housing and a laser beam oscillation device elastically mounted within the housing. The laser beam oscillation device includes an elongated support stand which extends substantially vertically within the housing and through an opening in the top of the housing, and a laser beam resonator such as a $CO_2$ laser is mounted on the support stand to provide a laser beam having an optical axis. A laser beam transmitting arrangement is connected to the support stand coaxially with the optical axis of the laser beam. As a result of this construction, the laser device occupies significantly less floor area within an operating room, and can easily be moved about while maintaining optical alignment at all times.

3 Claims, 5 Drawing Figures

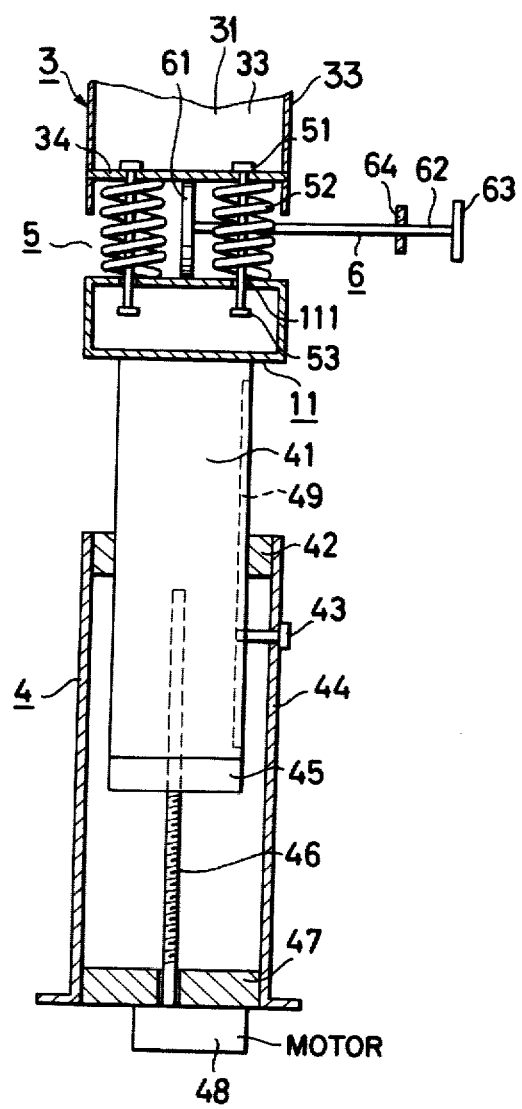

LASER DEVICE

BACKGROUND OF THE INVENTION

1. Field of the Invention

The present invention relates to a laser device, particularly to a laser device for surgery.

2. Description of Prior Art

As is widely known, conventional surgical laser devices are generally classifiable as one of two kinds of systems, namely:

(A) a system (hereinafter called System A) in accordance with which a laser beam oscillation device is secured to and extends horizontally on the system housing, and laser beam transmission devices such as a multiply manipulator which includes multiply articulated mirrors to lead the laser beam, flexible wave guide, optical fiber and the like are fixed to an opening in the device through which the laser beam is emitted; and (B) another system (hereinafter called System B) in accordance with which a laser beam oscillation control device and the laser beam oscillation device are arranged in a housing, and a laser beam transmission device such as the above mentioned multiply manipulator, flexible wave guide, optical fibers and the like are fixed to an opening in the housing through which the laser beam is emitted.

In case of the above System A, even if the total length of the laser beam oscillation device for producing a laser beam output (50–100 W) necessary for a surgical laser device is cut short by adopting a folded construction for the resonator, it is generally as long as about 1.5 m. Further, the area of the floor to be occupied with the housing containing the laser beam oscillation control device necessary for obtaining the above laser beam output is generally as large as about 80 cm × 100 cm.

When an operation is carried out with a surgical laser device having the construction and the dimensions as mentioned above in accordance with System A, the housing and the laser beam oscillation device have little effect on the working area of the surgeon. However, considering the fact that the floor area of the operating room is generally as large as 6 m × 6 m, the space of the operating room occupied by the surgical laser device is so large that the working area for attendants such as assistant doctors, nurses and the like is largely restricted.

Further, in case of the surgical laser device in accordance with System A, the above laser beam oscillation device is firmly secured above the housing, so that the position of the center of gravity is high. The optical system consisting of the above laser beam oscillation device and the above laser bean transmission device is thus often brought out of alignment due to shocks or vibrations during transportation of the system, resulting in undersirable changes of the laser beam output.

Further, in case of the device in accordance with System A, the horizontally arranged laser beam oscillation device is supported by means of a single vertical shaft at the center, so that the moment due to the weight of the laser beam oscillation device works upon both ends vertically downward. Thus, the support stand holding the laser beam oscillation device is distorted so as to accelerate warping of the optical alignment. Further, it goes without saying that the large space occupied with the surgical laser device in accordance with System A and its arrangement make transportation of the device all the more difficult.

In accordance with the System B, in the housing containing the laser beam oscillation control device, the laser beam oscillation device is vertically arranged. The laser beam emitted out of the laser beam emitting opening at the upper end of the laser beam oscillation device is transmitted up to an end piece connected to an end member of the laser beam transmission device such as a multiply manipulator secured to the ceiling directly above the laser beam emitting opening.

The construction of the surgical laser device in accordance with the System B is characterized in that the whole laser beam oscillation device including a discharge tube is vertically arranged in the housing, and that the laser beam transmission device is mechanically and firmly connected to the top of the above housing. Consequently, the height of the housing is about 2 m, and the total height including the laser beam transmission device projecting above the housing is 2.3 m–2.5 m.

Further, in the surgical laser device in accordance with the System B, the laser beam oscillation device and the laser beam transmission device are arranged separately from each other. Thus, due to thermal distortion, aging and mechanical deformation of the housing or the shocks, and vibration and the like during transportation, the optical axis of the laser beam oscillation device often goes out of coincidence with that of the laser beam transmission device. This lowers the laser beam output, which is undesirable. Further, as mentioned above, the surgical laser device is so high that transportation of the device often becomes impossible, the door lintel of the operating room becoming an obstacle.

As is widely known, generally it is necessary that communication among the doctor, the assistant doctors and the nurses should be carried out smoothly at the time of an operation. It is therefore believed that the height of the appliances equipped in the operating room should be limited to a height at least lower than the human eye, preferably 1 m.

Taking the above into consideration, the device in accordance with the System B, whose housing is as high as or higher than 2 m, serves to hinder communication among the persons participating in the operation, which is not practical.

In the case of a $CO_2$ laser device, which is generally used as a surgical laser device at present, the above mentioned manipulator is often used as a laser beam transmission device. In this case the necessary accuracy of the mirror to be used is remarkably high, so much so that it often occurs that the optical alignment is warped even from a slight shock, as so to lower the output extremely. Consequently, until now transportation of the surgical laser device after it has been once installed, is considered to be undesirable.

However, because more than one hour is generally needed for preparation for typical operations, it is desired that the appliances be movable from one to another operating room, in order to improve the efficient utilization of the appliances. Particularly for an appliance such as a surgical laser device whose field of application is very wide (for example, ordinary surgery, cranial surgery, plastic surgery, gynecological surgery, ophthalmic surgery and so on) and which is quite expensive, transportability is highly demanded.

The present invention is intended to offer a laser device, particularly a surgical laser device which can be realized in compact form so as to increase its portability, whereby the shortcomings of the conventional device as mentioned above are eliminated.

BRIEF DESCRIPTION OF THE DRAWINGS:

FIG. 3 shows an enlarged section of a vibration absorber together with a lifting device.

DESCRIPTION OF PREFERRED EMBODIMENTS:

Below, the present invention will be explained in detail in accordance with the drawings of the embodiment of the present invention.

Figure 1:
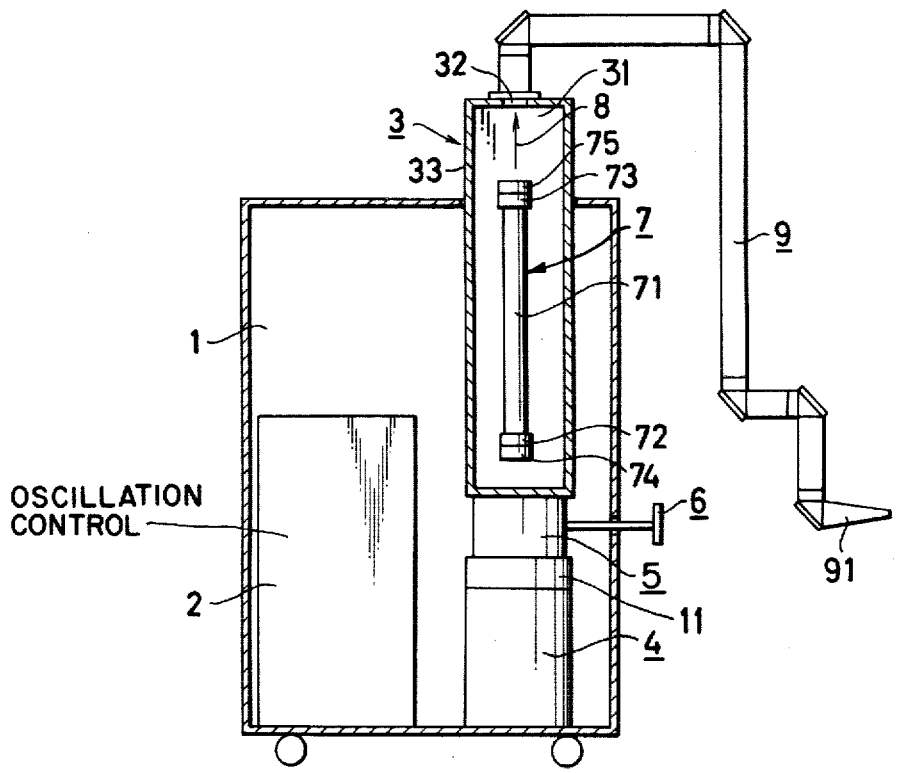
FIG. 1 shows a partial section through an embodiment of the present invention.

FIG. 1 shows a partial section through an embodiment of the present invention. In the housing 1, the laser beam oscillation control device 2 is contained. The laser beam oscillation device 3 consists of a support stand 31, a laser beam resonator 7, and a cylindrical body 33.

It is preferable that the lower end of the vertically arranged laser beam oscillation device 3 be secured on the bottom surface of the housing 1 through a vibration absorber 5 and a lifting device 4. On the other hand, the upper part of the laser beam oscillating device 3 projects through the opening provided in the ceiling of the housing 1. The vibration absorber 5 is provided with a locking handle 6 for checking the vibration absorbing efficiency.

The support stand 31 contained in the cylindrical body 33 includes a cast construction with, for example, a H-shaped profile, whose section perpendicular to the body axis has more than one axis of symmetry. On the support stand 31, mirror holders 72 and 73 are secured. In case the $CO_2$ laser is used as a laser beam resonator, an output mirror 75 is held by a mirror holder at one end of the laser tube 71, and a totally reflecting mirror 74 is held by a mirror holder 72 at the other end of the tube 71, thus constituting the laser resonator 7.

At the upper end of the support stand 31, a laser beam emitting opening 32 is provided so as to allow the passage of an output laser beam 8. Directly at the laser beam emitting opening 32 provided in the support stand 31, the laser beam transmission device 9 is secured. As the laser beam transmission device 9, a conventional multiply articulated mirror type manipulator, flexible wave guide, optical fiber and the like are generally made use of.

Figure 2A:
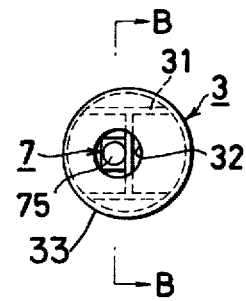
FIG. 2A shows an end view of a support stand in the laser beam oscillation device shown in FIG. 1.
Figure 2B:
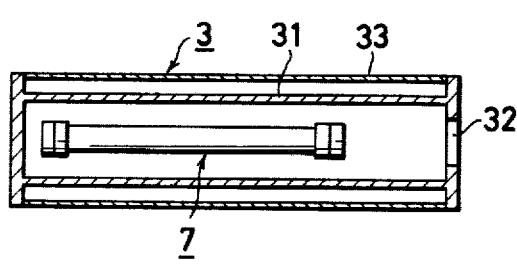
FIG. 2B shows a section along line B—B in FIG. 2A.

FIGS. 2A and B show the construction of an embodiment of the support stand.

The, the support stand 31 is contained in a cylindrical body 33 and is of a H-shaped profile construction, whose upper and lower portions are made flat to form upper and lower end plates, respectively. In the flat upper end plate, the laser beam emitting opening 32 is provided. The laser beam resonator 7 is secured in such a manner that the output laser beam 8 from the output mirror 75 is emitted through the laser beam emitting opening 32 in the flat upper end of the support stand 31, so that its optical axis coincides with that of the laser beam transmission device 9. In order to avoid distortion such as thermal deformation from taking place in the support stand 31, the larger the number of axes of symmetry in the plane perpendicular to the axis of the support stand 31, the more effective is the avoidance of distortion. It is most ideal that the laser resonator 7 be secured in a cylindrical pipe. However, it is extremely difficult to arrange the laser beam resonator 7 in such a cylindrical pipe.

As a modification, the support stand 31 may be made of alloy tubes or may be made of Invar alloy bars, welded together so as to have more than one axis of symmetry. The Invar alloy is preferable because of its minimal susceptibility to thermal distortion.

FIG. 3 shows an embodiment of the vibration absorber 5 and the lifting device 4. On bottom plate 34, at the lower end of the support stand 31, a plural number of pins 51 are each secured at one end, while at the upper end of the lifting device 4, a hollow stand seat 11 is secured. Between the stand seat 11 and the bottom plate 34, springs 52 are provided, each spring 52 surrounding a different one of the pins 51. Each of the pins 51 penetrates into the interior of the stand seat 11 through a slide hole 111 in an upper end plate of the stand seat 11, and a stop member 53 is secured at the other end of each pin 51 at a certain determined distance from the upper end plate of the stand seat 11.

Between the bottom plate 34 of the support stand 31 and the stand seat 11 there is provided a long elliptical cam plate 61. One end of a shaft 62 is secured to the cam plate 61 while the other end of the shaft 62 is led out of the housing 1, and is provided with a handle 63. Further, the shaft 62 is supported by a slide bearing 64 secured in the housing 1. Owing to the above mentioned construction, rotation of the handle 63 causes the long part of the cam plate 61 increase the distance between the laser oscillation device 3 and the stand seat 11 so as to restrict the shock absorbing efficiency of the springs 52. This corresponds to a locked state. This locking device can generally be made use of during a surgical laser operation. This vibration absorber 5 is not necessarily limited in application to the above embodiment in which the springs 52 are made use of. Any elastic material such as rubber can also be used. Namely, it is sufficient that vibration, shock and the like from outside cannot be transmitted to the laser resonator 7, the beam transmission device 9 and other components.

Below, the lifting device 4 will be explained in detail. In an external cylinder 44, a slide bearing 42 and a bearing 47 are secured respectively at the upper part and at the lower part of the cylinder 44. A motor 48 is secured at the lower end of the above bearing 47. At the lower end of an internal cylinder 41 a nut 45 is provided so as to be inserted in the external cylinder 44 through the slide bearing 42.

A screw 46 is inserted into the above nut 45, the lower end of the screw 46 passing through the bearing 47 and connecting to the motor 48. Further, one end of a pin 43 which is screwed into the above external cylinder 44 engages a groove 49 provided longitudinally along the side of the internal cylinder 41 so as to prevent rotation of the internal cylinder 41. According to the above construction, along with the rotation of the screw 46 by means of the motor 48, the internal cylinder 41 is displaced either in an upward or a downward direction.

The lifting device 4 serves to make the height of the operation stand relative to that of an end piece 91 of the laser beam transmission device 9 (FIG. 1) optimum, and at the same time to lower the total height of the surgical laser device during transport. Consequently, in case the operating condition of the surgical laser device is fixed, and the total height of the surgical laser device causes no problem in transport, the lifting device 4 can be replaced with a general fixed stand without any problem.

In this case, it is preferable that the uppe part of the above laser beam oscillation device 3 be fixed to the edge of the opening of the housing 1 through an antivibration holding member such as an O-ring of elastic material. Due to such means, the optical system including the laser beam resonator 7, beam transmission device 9 and the like will be less influenced by vibrations.

As a further modification, the laser beam oscillation device 3 can be supported elastically by supporting arms extending from the inside walls of the housing 1, with shock-absorbing members such as rubber or springs therebetween, without using a fixed stand or the lifting device 4.

The oscillation wave length of the $CO_2$ laser falls in the infrared beam range. Consequently, in order to offer a more convenient surgical laser device, an embodiment in accordance with which besides a visible guide beam, a beam shutter and a power meter are arranged on the support stand 31, can be realized. In this case, it is essential that the axis of the visible guide beam coincide with that of the $CO_2$ laser beam. In order to fulfill such a condition, it is sufficient that the beam mixing part, consisting of a plural number of mirrors, be secured on the support stand 31.

Further, in case the laser beam output is comparatively large ($\fallingdotseq$100 W) or the total length of the laser beam oscillation device 3 is desired to be cut short, the total length of the laser beam resonator 7 can be cut by about half if a folded construction is applied. In this case, the resonator can be realized by adding a center bending mirror holder and two center bending mirrors to the resonator shown in FIG. 1, as is already well known.

Figure 4:
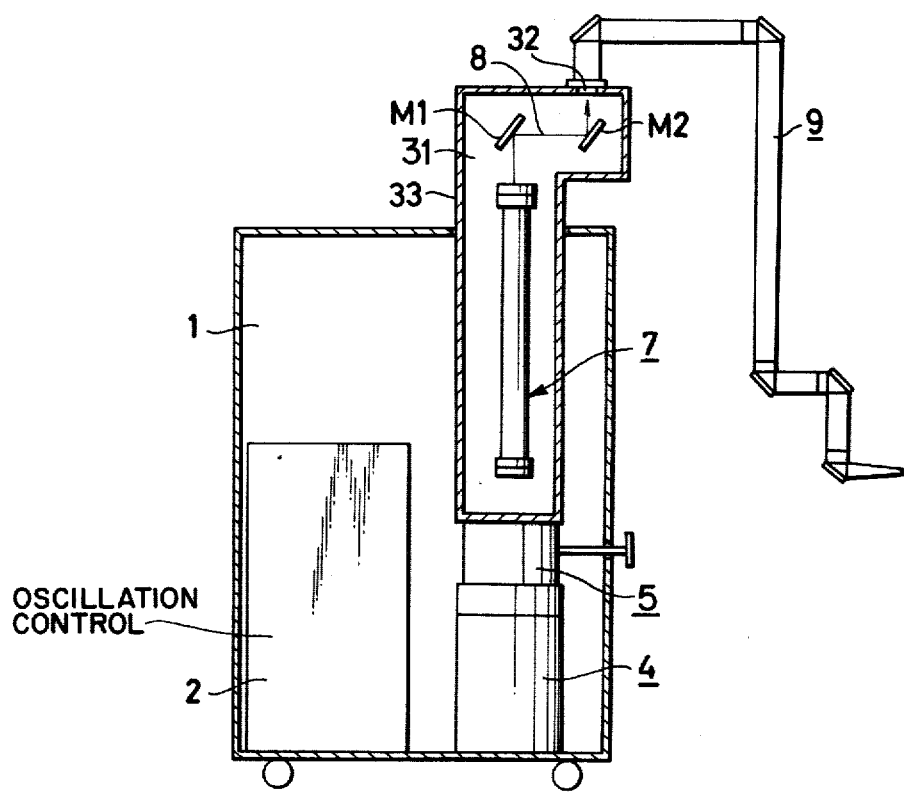
FIG. 4 shows a partial section through another embodiment of the present invention.

FIG. 4 shows a partial section of a second embodiment of the present invention. In this case, a L-shaped profile is adopted for the support stand 31. The laser beam 8 emitted from the laser beam resonator 7, which beam has been led to the laser beam emitting opening 32 by means of the reflecting mirrors M1 and M2, is led to the desired position by means of the beam transmission device 9.

Although not shown in the drawing, in the case of the present embodiment, a L-shaped profile can also be adopted to the laser beam resonator 7 in such a manner that the resonator 7 can move along the support stand 31. In this case the center bending mirrors can be provided at the folded part of the laser beam resonator 7.

Because in the present invention, as is explained above, the laser beam oscillation device 3 is provided vertically so as to project through the ceiling of the housing 1, the height of the housing can be freely selected to some extent in conformance with the laser beam oscillation control device. Thus, the height of the housing 1 can be made smaller than 1.2 m for the ordinary device. Further, the area of the floor occupied with the present laser device is determined only by the area of the housing 1 containing the laser beam oscillation control device 2, the lifting device 4 and the like. The above floor area can be made as large as in case of the System A or B, or smaller, namely, about 60 cm × 70 cm.

As mentioned above, the height of the housing 1 of the present surgical laser device can be kept small so that at the time of the medical operation there is no obstacle between the operator and the attendant, in such a manner that communications between them can be carried out smoothly. Further, the total height of the device can be decreased down to about 1.9 m by means of the lifting device 4 during transportation, and the portability of the laser device can be remarkably improved.

Further, vibrations such as shocks or vibrations produced through the housing 1 during transportation of the surgical laser device are absorbed by the springs 52 in the vibration absorber 5 so they are not transmitted to the laser beam oscillation device 3.

Further, the support stand 31 consisting of one construction whose cross section perpendicular to the axial direction presents more than one axis of symmetry is applied to the laser beam oscillation device 3 and arranged vertically on the housing 1 through the absorber 5.

It is clear from the above that as has been pointed out with reference to the System A, the support stand 31 is scarcely deformed by means of the moment due to the proper weight of the support stand 31, nor by means of thermal distortion due to the variation of the ambient conditions.

In consequence, the optical system consisting of the laser beam oscillation device 3 and the laser beam transmission device 9 is not influenced by shocks and vibrations from the housing 1, or the variation of the ambient conditions, in such a manner that the optical alignment is always kept in order over a long period of time.

As mentioned above, the surgical laser device of the present invention can be realized compactly, while its portability is much improved. The optical system is highly stabilized so as not to be brought out of order, which is a feature that cannot be realized in the conventional surgical laser device. Thus, the present invention contributes greatly to the development of the surgical laser device in the medical field.

What is claimed is:

1. A laser device which comprises:
   a housing having a top end with a first opening in this top end;
   a laser beam oscillation device elastically supported in the housing;
   said laser beam oscillation device including:
   an elongated support stand arranged substantially vertically in the housing and having an upper end projecting through the first opening in said top end of said housing, said support stand having at least one axis of symmetry in its cross section perpendicular to its longitudinal axis;
   a laser beam resonator mounted on the support stand for providing a laser beam having an optical axis; and means for transmitting the laser beam emitted from the laser beam resonator, said transmitting means being connected to the support stand coaxially with the optical axis of the laser beam.

2. A laser device according to claim 1, which further comprises:
   lifting means within said housing for moving the support stand vertically in the housing; and
   a vibration absorber provided between the support stand and the lifting means.

3. A laser device according to claim 1, in which the support stand has at its upper end a second opening for passing the laser beam emitted from the laser resonator.

* * * * *